United States Patent
Nakayama (10) Patent No.: US 10,001,460 B2
(45) Date of Patent: *Jun. 19, 2018

(54) PHASING ADDER AND ULTRASOUND PROBE

(71) Applicant: Konica Minolta, Inc., Tokyo (JP)

(72) Inventor: Yuta Nakayama, Ichikawa (JP)

(73) Assignee: KONICA MINOLTA, INC., Tokyo (JP)

(*) Notice: Subject to any disclaimer, the term of this patent is extended or adjusted under 35 U.S.C. 154(b) by 179 days.

This patent is subject to a terminal disclaimer.

(21) Appl. No.: 14/325,881

(22) Filed: Jul. 8, 2014

(65) Prior Publication Data

US 2015/0013466 A1    Jan. 15, 2015

(30) Foreign Application Priority Data

Jul. 10, 2013  (JP) .................................. 2013-144297
Jul. 7, 2014   (JP) .................................. 2014-139424

(51) Int. Cl.
*G01N 29/24*   (2006.01)
*H01L 27/20*   (2006.01)
(Continued)

(52) U.S. Cl.
CPC ....... *G01N 29/2437* (2013.01); *A61B 8/4483* (2013.01); *A61B 8/5207* (2013.01);
(Continued)

(58) Field of Classification Search
CPC ............... G01N 29/2437; G01N 29/34; G01N 29/2481; G01N 29/2468; G06G 7/14; G10K 11/346
See application file for complete search history.

(56) References Cited

U.S. PATENT DOCUMENTS 4,152,678 A * 5/1979 Shott .................... G10K 11/345
                                                    333/150
4,882,714 A    11/1989 Tanigawa
(Continued)

FOREIGN PATENT DOCUMENTS

EP          0177802 A2 *  4/1986  ............. H01L 27/20
JP       2001-292496 A    10/2001
(Continued)

OTHER PUBLICATIONS

English translation of EP 0177802.*
(Continued)

*Primary Examiner* — Paul West
*Assistant Examiner* — Xin Zhong
(74) *Attorney, Agent, or Firm* — Lucas & Mercanti, LLP (57) ABSTRACT

A phasing adder and an ultrasound probe are disclosed. According to one implementation, the phasing adder includes a delay charge transferring unit and a delay adding unit. The delay charge transferring unit obtains signal charge in an amount obtained without amplifying according to charge generated in each of a plurality of piezoelectric elements. Each of the plurality of piezoelectric elements includes a piezoelectric body to generate charge according to sound pressure of input ultrasound. The delay charge transferring unit holds the signal charge for a predetermined amount of time. The delay adding unit executes phasing adding of an amount of the signal charge held for the predetermined amount of time in the delay charge transferring unit.

14 Claims, 11 Drawing Sheets

(51) Int. Cl.
  *G06G 7/14* (2006.01)
  *G01N 29/34* (2006.01)
  *G01N 29/36* (2006.01)
  *G10K 11/34* (2006.01)
  *B06B 1/02* (2006.01)
  *B06B 1/06* (2006.01)
  *A61B 8/08* (2006.01)
  *A61B 8/00* (2006.01)

(52) U.S. Cl.
  CPC .......... *B06B 1/0215* (2013.01); *B06B 1/0622* (2013.01); *G01N 29/2481* (2013.01); *G01N 29/34* (2013.01); *G01N 29/36* (2013.01); *G06G 7/14* (2013.01); *G10K 11/346* (2013.01); *H01L 27/20* (2013.01); *A61B 8/4405* (2013.01); *A61B 8/4472* (2013.01); *G01N 2291/012* (2013.01); *G01N 2291/106* (2013.01)

(56) References Cited

U.S. PATENT DOCUMENTS

| | | | | |
|---|---|---|---|---|
| 5,085,081 | A * | 2/1992 | Ohno | G01H 3/125 73/606 |
| 6,113,547 | A * | 9/2000 | Catallo | G01S 7/003 600/459 |
| 2008/0294050 | A1* | 11/2008 | Shinomura | A61B 8/00 600/459 |
| 2009/0303838 | A1* | 12/2009 | Svet | G01N 29/075 367/157 |
| 2015/0260691 | A1* | 9/2015 | Nakayama | G01N 29/2481 73/661 |

FOREIGN PATENT DOCUMENTS

| | | |
|---|---|---|
| JP | 2002-530174 A | 9/2002 |
| JP | 2005-270423 A | 10/2005 |
| JP | 2008-545501 A | 12/2008 |
| WO | 00/31562 A2 | 6/2000 |
| WO | 2006/006460 A1 | 1/2006 |
| WO | 2007000567 A1 | 1/2007 |

OTHER PUBLICATIONS

International Search Report; International Application No. 201410327914.9: dated Dec. 3, 2015; Applicant: Konica Minolta, Inc.; Title: Phasing adder and ultrasound probe; total of 9 pages.
English translation of International Search Report aobve; Total of 10 pages.
Extended European Search Report dated Feb. 26, 2015 for the corresponding European Patent Application No. 14176427.4.
Office Action dated Aug. 11, 2016 from the corresponding Chinese Application; Patent Application No. 201410327914.9; Applicant: Konica Minolta, Inc.; Title: Phasing Adder and Ultrasound Probe; English translation of Office Action; Total of 18 pages.
Office Action dated Apr. 1, 2017 from corresponding Chinese Patent Application No. 201410327914.9; Applicant: Konica Minolta, Inc.; English translation of Office Action: Total of 16 pages.
Notification of Refusal dated Mar. 6, 2018 from corresponding Japanese Patent Application No. JP 2014-139424 and English translation.

* cited by examiner

PHASING ADDER AND ULTRASOUND PROBE

BACKGROUND

Field of the Invention

The present invention relates to a phasing adder and an ultrasound probe.

Description of Related Art

Conventionally, there is an ultrasound diagnostic apparatus which irradiates ultrasound inside a subject, receives the reflected wave and analyzes the reflected wave to examine an internal structure. With ultrasound diagnosis, it is possible to examine the subject in a non-destructive, non-invasive form, and is therefore used widely for various purposes such as medical examination or internal examination of a building.

In an ultrasound diagnosis apparatus, the received ultrasound is converted to an electric signal according to its intensity and is obtained. In receiving the ultrasound, a transducer such as a piezoelectric element is used. The mechanical deformation (expansion and contraction) of the piezoelectric element by sound pressure of the ultrasound is converted to an electric signal (charge amount) according to the deformation amount and is detected. Here, since there is a difference in the timing that the large number of piezoelectric elements receive the reflected wave from the examination target point, the data regarding the reflected wave from the examination target point can be obtained by setting and adding a delay time suitable for each element.

Lately, consumption of electric power of the ultrasound diagnostic apparatus is increasing because of increase of the number of piezoelectric elements for receiving and increase of a sampling rate of receiving data due to images becoming highly accurate. Japanese Patent No. 4557575 discloses the following technique. An electric signal is selectively input in any CCD (Charge Coupled Device) delay element provided in parallel with each piezoelectric element with a different transfer gate number. Charge data regarding the plurality of piezoelectric elements are delayed a suitable number of steps and added by phasing adding. Then, the above data is converted to voltage data in one of the FGA (Floating Gate Amplifier). With this, it is possible to reduce the number of FGA used on each piece of data before phasing adding from the conventional number and to reduce electric power consumption.

However, the intensity of the electric signal obtained by the transducer according to the intensity of the ultrasound received in ultrasound diagnosis is very small. Therefore, normally such electric signal is amplified right after this is obtained by the transducer and then transferred and processed. Here, if a low noise amplifier (LNA) is used to amplify the signal without increasing the noise level, the supply electric current increases according to the noise reduction amount. Therefore, conventionally, there is a problem that it is difficult to achieve both of the following, enhancing the signal-noise ratio (SNR) and suppressing electric power consumption.

SUMMARY

The present invention has been made in consideration of the above problems, and it is one of main objects to provide a phasing adder and an ultrasound probe so as to be able to efficiently suppress electric power consumption while maintaining SNR of the obtained signal.

In order to achieve at least one of the above-described objects, according to an aspect of the present invention, there is provided a phasing adder including:

a delay charge transferring unit which obtains signal charge in an amount obtained without amplifying according to charge generated in each of a plurality of piezoelectric elements each including a piezoelectric body to generate charge according to sound pressure of input ultrasound and which holds the signal charge for a predetermined amount of time; and a delay adding unit which executes phasing adding of an amount of the signal charge held for the predetermined amount of time in the delay charge transferring unit.

Preferably, in the phasing adder, the amount of the signal charge corresponds to charge amount induced in an electrode provided on both edges of the piezoelectric body in which the charge is generated in the piezoelectric element.

Preferably, the phasing adder further includes, a switching unit including a source region connected to a predetermined bias voltage generating unit, and a gate electrode which determines a conductive state between the source region and the delay charge transferring unit, wherein, the gate electrode is connected to either one of electrodes provided on both edges of the piezoelectric body in which the charge is generated in the piezoelectric element; and the delay charge transferring unit obtains the signal charge from the source region based on potential of the gate electrode which changes according to the charge generated in the piezoelectric body.

Preferably, in the phasing adder the bias voltage is applied synchronized with a cycle of change of charge amount generated in the piezoelectric body.

Preferably, in the phasing adder, a CCD is used as the delay charge transferring unit.

Preferably, in the phasing adder, the delay charge transferring unit is connected to an electrode through an interposer, the electrode provided on both edges of the piezoelectric body in which the charge is generated in the piezoelectric element.

Preferably, an ultrasound probe includes:

a phasing adder described above;

the piezoelectric element connected to the phasing adder;

a signal amplifying unit which amplifies a charge amount processed by phasing adding as the voltage signal; and a signal output unit which outputs the amplified voltage signal.

Preferably, in the ultrasound probe, the signal output unit includes a wireless communication unit which outputs the signal to an external device wirelessly.

Preferably, the ultrasound probe further includes:

a transmitting driving unit which outputs an ultrasound with a predetermined wavelength from the piezoelectric element; and a transmitting/receiving switching driving unit which selectively connects the piezoelectric element to either one of the transmitting driving unit or the delay charge transferring unit according to a control signal.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

Below, an embodiment of the present invention is described with reference to the drawings.

Figure 1:
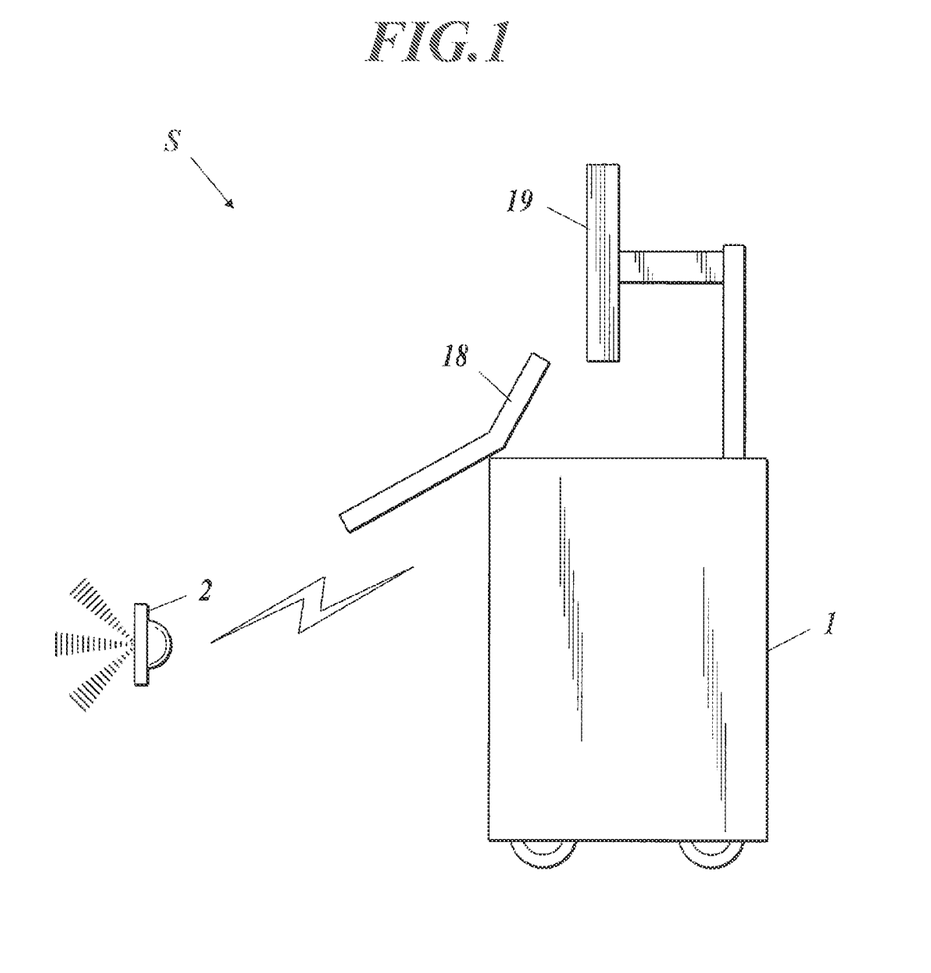
FIG. 1 is a diagram showing an entire configuration of an ultrasound diagnostic apparatus including an ultrasound probe according to an embodiment of the present invention.

FIG. 1 is a diagram showing an entire configuration of an ultrasound diagnostic apparatus S including an ultrasound probe 2 according to the present embodiment.

The ultrasound diagnostic apparatus S includes an ultrasound diagnostic apparatus main body 1 and the ultrasound probe 2. The ultrasound diagnostic apparatus main body 1 includes an operation input unit 18, an output display unit 19, and a control unit and a communication unit which are not shown. Based on input operation from outside on a keyboard or a mouse of the operation input unit 18, the control unit of the ultrasound diagnostic apparatus main body 1 outputs a control signal to the ultrasound probe 2 through the communication unit so that the ultrasound probe 2 emits ultrasound. Moreover, the control unit of the ultrasound diagnostic apparatus main body 1 receives input detecting data of the ultrasound from the ultrasound probe 2, performs various processing, and displays the result, etc. as necessary on a liquid crystal screen of the output display unit 19.

The ultrasound probe 2 transmits ultrasound (here, about 1 to 30 MHz) to the subject, and among the transmitted ultrasound, the wave which is reflected on the subject and returned is received as the reflected wave (echo). The ultrasound probe 2 communicates the control signal and data with the ultrasound diagnostic apparatus main body 1 by wireless communication.

Figure 2:
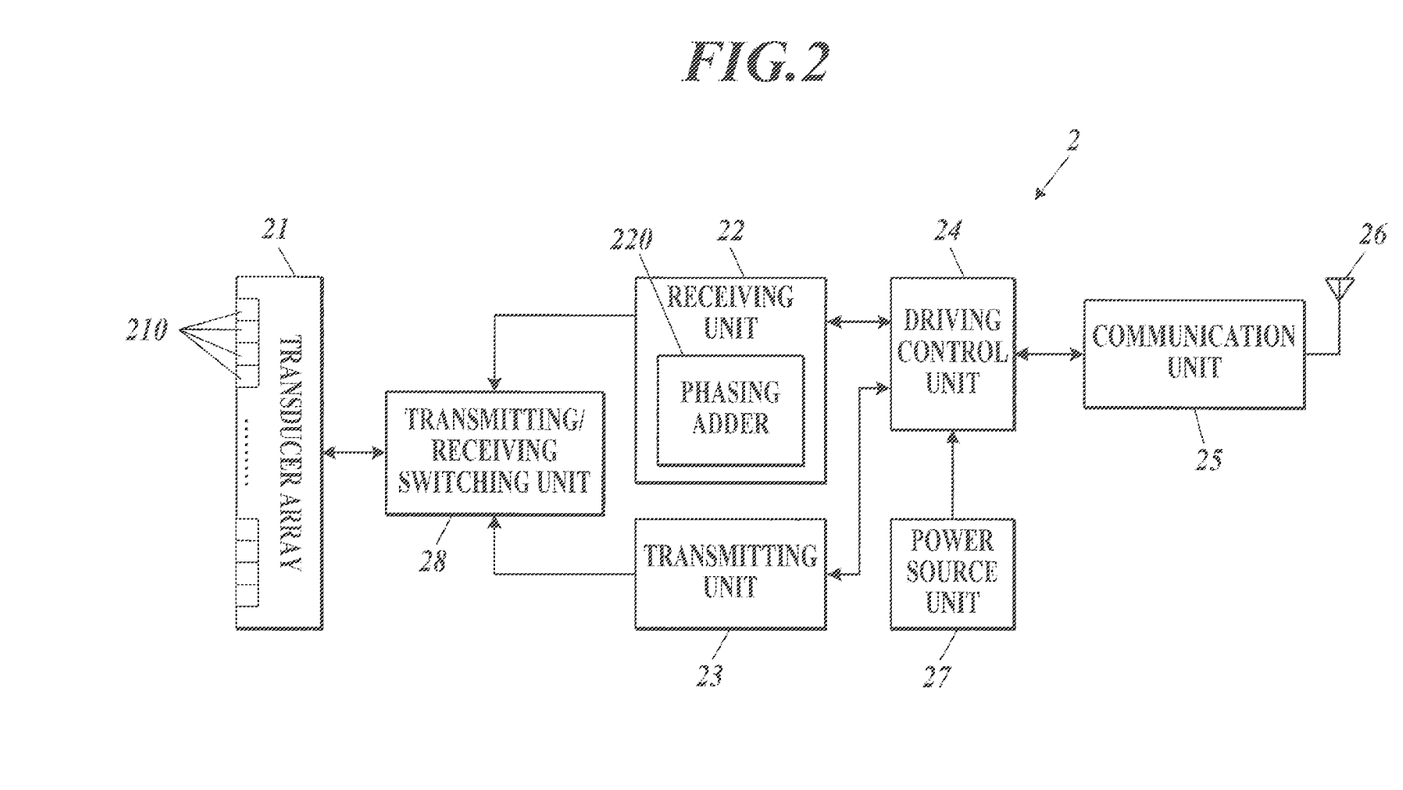
FIG. 2 is a block diagram showing an internal configuration of the ultrasound probe.

FIG. 2 is a block diagram showing an internal configuration of the ultrasound probe 2.

The ultrasound probe 2 includes a transducer array 21, a receiving unit 22, a transmitting unit 23 (transmitting driving unit), a driving control unit 24, a communication unit 25 (signal output unit, wireless communication unit), an antenna 26, a power source unit 27, and a transmitting/receiving switching unit 28 (transmitting/receiving switching driving unit).

The transducer array 21 is an array of a plurality of transducers 210 including a piezoelectric element including a piezoelectric body and an electrode in which charge appears by deformation (expansion and contraction) of the piezoelectric body and which is provided in each edge. For example, such transducers 210 are arranged in a one-dimensional array in a predetermined direction. A voltage pulse (pulse signal) is added to the transducer 210 and the piezoelectric body is deformed. The ultrasound is transmitted in an amplitude according to a size of the voltage. When ultrasound of a predetermined frequency band is transmitted to the transducer 210, the sound voltage changes (vibrates) a thickness of the sound body of the transducer element, and charge according to the change amount appears. Charge in an amount according to the above charge is induced in the electrodes on both edges of the piezoelectric element.

The piezoelectric member used in the piezoelectric body of the transducer 210 is, for example, PZT (lead zirconate titanate). Alternatively, any one of the following other various piezoelectric members can be used, for example, single crystals such as $LiNbO_3$, $LiTaOc$, $KNbOc$, crystal, etc., polycrystals such as Pb $(Mg_{1/3}Nb_{2/3})O_3$, (Pb, Sm) $TiO_3$, etc., relaxor ferroelectric such as PMN-PT (lead magnesium niobate-lead titanate), PZN-PT (zinc lead niobate-lead titanate), etc., an organic member such as PVDF (polyvinylidene fluoride) or PVDF type copolymer, polyvinilidene cyanide or vinylidene cyanide type copolymer, odd number nylon such as nylon 9 or nylon 11, aromatic nylon, alicyclic nylon, polyactate, polyhydroxy carboxylic acid such as PHB (polyhydroxy butyric acid), cellulose derivative, polyurea, or the like. Alternatively, a composite material using both inorganic piezoelectric material and organic piezoelectric material can be used.

The ultrasound probe 2 of the present embodiment includes, for example, 192 transducers 210 in the transducer array 21. Alternatively, each transducer 210 can be arranged in a two dimensional array to obtain a three dimensional ultrasound image. The number of transducers 210 can be suitably set according to various conditions such as resolution, electric power consumption, and data transferable speed. The ultrasound probe 2 can employ either one of the electronic scanning method or mechanical scanning method. Alternatively, as the scanning method, any of the following methods can be employed, for example, a linear scanning method, a sector scanning method or a convex scanning method. The band width in the ultrasound probe 2 can be arbitrarily set.

The ultrasound diagnostic apparatus S can be used by combining the ultrasound diagnostic apparatus main body 1 with any one of a plurality of different ultrasound probes 2 according to the diagnostic target.

The receiving unit 22 converts the charge induced with the input of the ultrasound in each transducer 210 of the transducer array 21 to a voltage signal according to the charge amount, amplifies the voltage signal, and then outputs the data digitally converted with a predetermined sampling frequency as the receiving signal. The receiving unit 22 includes a phasing adder 220, an LNA (Low Noise Amplifier) 223 (signal amplifying unit), and an ADC (analog/digital converter) 224 (see FIG. 5). The receiving unit 22 is described later.

The transmitting unit 23 outputs to the transducer 210 a voltage pulse signal to output the ultrasound at a predetermined amplitude and frequency from the transducer 210 specified according to the control signal from the driving control unit 24.

Based on the control signal from the driving control unit 24, the transmitting/receiving switching unit 28 connects either the transmitting unit 23 or the receiving unit 22 to the transducer array 21 and allows the transmitting unit 23 to transmit the voltage pulse signal regarding driving of the transducer 210 or allows the receiving unit 22 to transmit an electric signal regarding the ultrasound input in the transducer 210.

According to the control signal input from the communication unit 25, the driving control unit 24 transmits a control signal to the transmitting/receiving switching unit 28 and switches the setting of the connection to the transducer array 21 between the transmitting unit 23 and the receiving unit 22. Then, the driving control unit 24 controls the transmitting unit 23 to output the ultrasound from the transducer 210 or controls the receiving unit 22 to output from the transducer array 21 the charge signal according to the ultrasound input to each transducer 210 during the ultrasound output to obtain the receiving signal from the receiving unit 22. The driving control unit 24 controls the communication unit 25 and the antenna 26 to transmit the receiving signal of the ultrasound to the ultrasound diagnostic apparatus main body 1.

The communication unit 25 is a communication interface for transmitting and receiving control signals and obtained data with the ultrasound diagnostic apparatus main body 1. A communication interface for communication among various well-known wireless communication methods is used. As such wireless communication methods, there are communication methods in frequency bands based on communication standards with which sufficient data transfer speed from the ultrasound probe 2 to the ultrasound diagnostic apparatus main body 1 can be achieved, for example, wireless LAN (IEEE 802.11n, etc.), BLUETOOTH (registered trademark) communication, and body area network (BAN; IEEE 802.15.6).

The antenna 26 transmits and receives communication radio waves when the communication unit 25 communicates wirelessly with the communication unit of the ultrasound diagnostic apparatus main body 1. The size and the shape of the antenna 26 depends on the frequency used in communication and the size of the ultrasound probe 2.

The power source unit 27 supplies electric power to each unit of the ultrasound probe 2 to operate the units. Although not limited, the power source unit 27 includes a normal battery. Alternatively, the power source unit 27 can include a boosting circuit, and raise the output voltage of the battery to a suitable voltage according to the ultrasound output from the transducer 210, and supply the electric power to the transducer 210 after raising the voltage.

Next, the reception of the ultrasound in the ultrasound probe 2 of the present embodiment is described.

Figure 3:
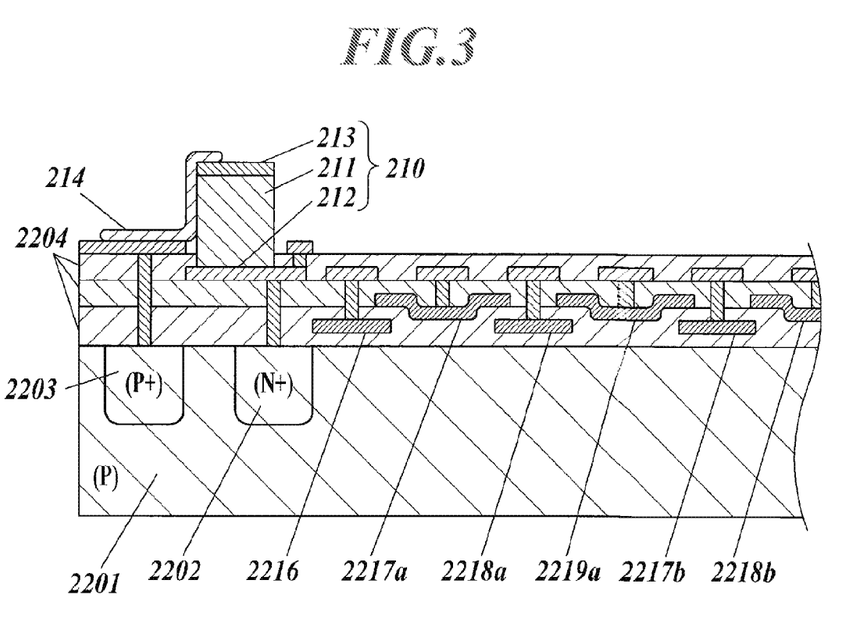
FIG. 3 is a cross-sectional diagram describing reception of ultrasound by the ultrasound probe.

FIG. 3 is a cross-sectional diagram describing the ultrasound reception in the ultrasound probe 2 of the present embodiment. The cross-section is a face cutting a semiconductor substrate 2201 at a face including one transducer 210 and a CCD 221 corresponding to the transducer 210.

The ultrasound probe 2 of the present embodiment is positioned connected to a circuit where the transducer 210 is provided on the semiconductor substrate 2201. The semiconductor substrate is a P-type substrate. An electrode 212 provided in one edge of a piezoelectric body 211 of the transducer 210 is connected to an N-type region 2202 provided on an upper face of the semiconductor substrate 2201. An electrode 213 provided on one edge of the piezoelectric body 211 is connected to the semiconductor substrate 2201 through a conductive member 214. The connecting portion is a P-type region 2203 with impurity concentration heightened by injecting impurity ion such as B (boron) so that electric current flows between the conductive member 214 and the semiconductor substrate 2201, and ohmic contact is formed with the metallic conductive member 214.

It is preferable that the electrodes 212 and 213 are conductive bodies with small electric resistance, and for example, aluminum is used. The solidifying point of aluminum under standard atmosphere is about 660° C. Layers of each region, electrode, and transducer 210 are formed in order on or above the semiconductor substrate 2201 in the ultrasound probe 2 of the present embodiment. Therefore, heat balance in later steps in forming the layer are influenced by the portions formed in earlier steps. In other words, when the circuit is formed on the semiconductor substrate 2201 and then the transducer 210 is formed, the piezoelectric phase (ferroelectric phase in the ferroelectric body) of the piezoelectric member needs to be formed with a temperature less than the solidifying point (for example, 650° C.)

The semiconductor substrate 2201 which is a P-type substrate and the N-type region 2202 are a diode structure with a P-N junction. The N-type region 2202 is a conductive region injected with impurity ion such as P (phosphorous) or As (arsenic). When the transducer 210 is deformed by the ultrasound and charge appears, charge with the opposite polarity is induced to the electrodes 212 and 213.

An insulating layer 2204 is provided above a region of the semiconductor substrate 2201, and a plurality of electrodes are arranged on the insulating layer 2204. An IG (input get) electrode 2216 provided on a side of the N-type region 2202, and transfer electrodes 2217a to 2219a, 2217b, and 2218b are included in these electrodes. A CCD (Charge Coupled Device) 221 is formed by these electrodes and a lower portion region of the electrode in the semiconductor substrate 2201. A signal charge (electron) introduced from the N-type region 2202 according to the charge induced in the electrodes 212 and 213 are sequentially transferred based on the voltage applied in order on each electrode.

FIG. 4A to FIG. 4D are diagrams describing the conveying process of the electron in the CCD 221. The vertical axis in the lower direction shows the potential in the electrode lower portion of the semiconductor substrate 2201 in relation with the position corresponding to each electrode (horizontal axis).

Figure 4A:
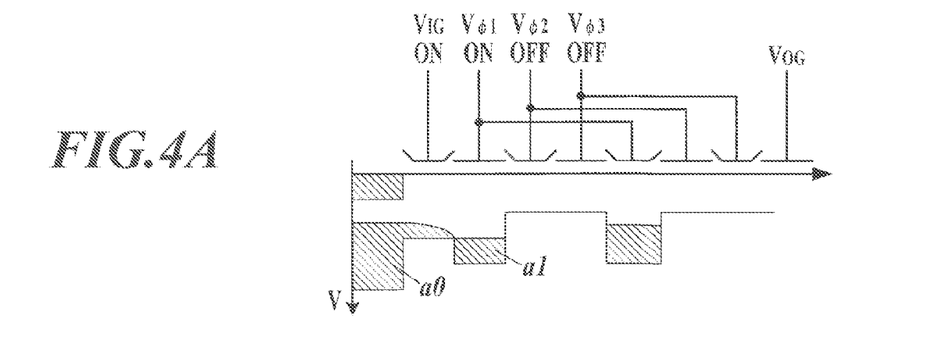
FIG. 4A is a diagram describing a conveying process of charge by a CCD.

If positive voltage VIG is applied to the IG electrode 2216 in a state where a positive voltage Vφ1 is applied to the transfer electrodes 2217a and 2217b and further when electrons are accumulated in the N-type region 2202 (a0, shaded portion), electrons from the N-type region 2202 pass a channel region formed in the lower portion of the IG electrode 2216 and flow into a potential well (a1) formed in the lower portion of the transfer electrode 2217a in the semiconductor substrate 2201 (FIG. 4A).

Figure 4B:
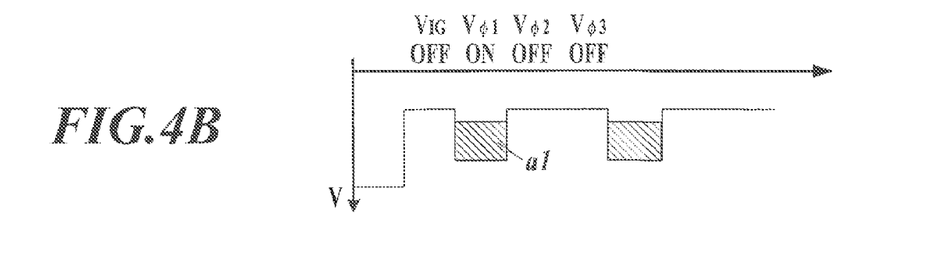
FIG. 4B is a diagram describing a conveying process of charge by a CCD.
Figure 4C:
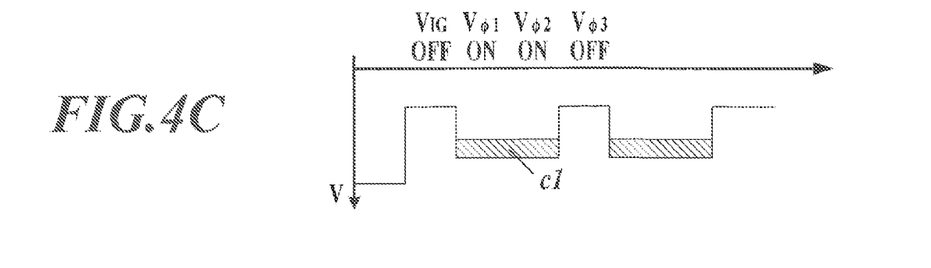
FIG. 4C is a diagram describing a conveying process of charge by a CCD.

Next, the positive voltage applied to the IG electrode 2216 is released, and the potential well (a1) is separated from the N-type region 2202 (FIG. 4B). Then, when the positive potential Vϕ2 is applied to the transfer electrodes 2218a and 2218b, the potential well (a1) spreads to the region of the transfer electrodes 2217a and 2218a (c1), and the electrons are distributed substantially evenly in the potential well (FIG. 4C).

Figure 4D:
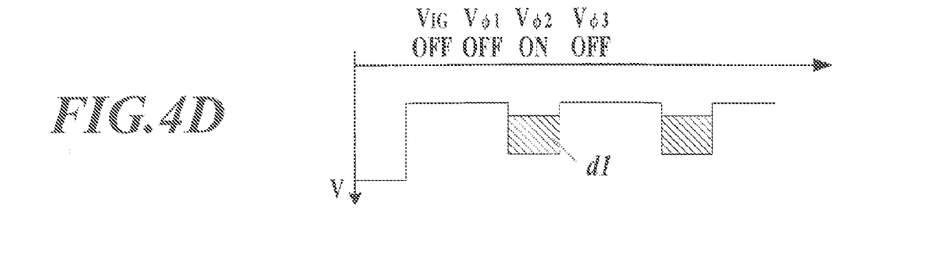
FIG. 4D is a diagram describing a conveying process of charge by a CCD.

Then, further, when the positive voltage applied to the transfer electrodes 2217a and 2217b is released, the potential well (c1) is narrowed to the region including only the lower portion of the transfer electrode 2218a, and with this, the electron in the lower portion of the transfer electrode 2217a is collected in the potential well (d1) formed in the lower portion of the transfer electrode 2218a (FIG. 4D). In other words, at this stage, the electrons in the potential well (a1) shown in FIG. 4B moves to the lower portion of one transfer electrode to the right. As described above, the CCD 221 shifts the position in the transfer electrode where the positive voltage is applied, and the electron trapped in the potential well is sequentially transferred.

The amount of charge trapped in the potential well can be selectively read out. Although not limited, the readout here does not directly take out charge trapped in the potential well, and is performed by mirroring in a non-destructive manner. In other words, according to such configuration, it is possible to read out the same data a plurality of times from a plurality of potential wells with different delay step numbers (delay time). The charge transferred to the potential well of the final transfer electrode in the CCD 221 is discharged grounded to the substrate according to the voltage VOG applied to the OG (output gate) electrode.

Figure 5:
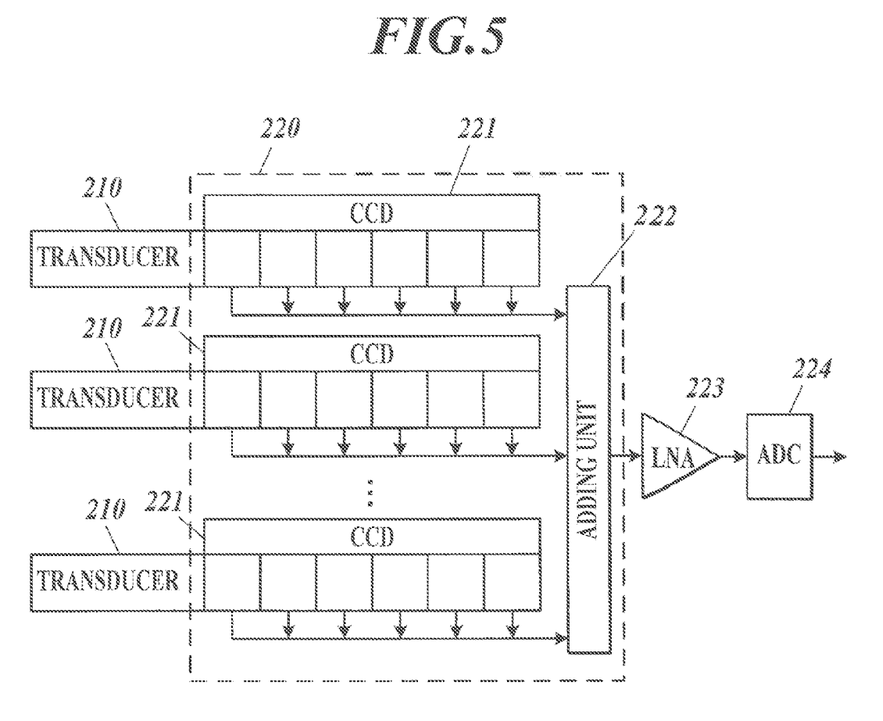
FIG. 5 is a diagram describing a phasing adder.

FIG. 5 is a block diagram describing a flow of data in the receiving unit 22.

The phasing adder 220 includes a plurality of CCD 221 (delay charge transferring unit) where each one transfers the charge obtained from each transducer 210, and an adding unit 222 (delay adding unit) which adds (phasing adding) the charge amount transferred at a predetermined stage by each CCD 221. The charge added in the phase adder 220 is converted to a voltage value and amplified by the LNA 223 (for example, floating diffusion). Then, the result is output to the ADC 224, and converted to a digital value in a predetermined sampling frequency.

As shown in FIG. 3 and FIG. 4A to FIG. 4D, in the phasing adder 220 of the present embodiment, charge in the amount corresponding to the charge induced to the electrodes 212 and 213 at both edges depending on the deformation of each transducer 210 is taken in without amplifying directly from the N-type region 2202 to the CCD 221. After transferring the taken in charge among the plurality of potential wells formed in the CCD 221, the charge is selectively read from any of the potential wells depending on the delay time. In other words, in the phasing adder 220, by setting the position of the potential well where the charge amount is read for each CCD 221, the delay step number regarding the phasing adding is set individually. The number of potential wells which can be formed in the CCD 221, in other words, the delay step number is suitably set. It is preferable that the number is not extremely large (for example, 10 steps or less), because as the number becomes larger, the loss of charge and the transfer electric power becomes greater.

The charge read from the plurality of CCD 221 corresponding to one adding unit 222 is added in the adding unit 222. The added charge amount is converted to a voltage value and then collectively amplified in the LNA 223. In other words, pieces of data obtained from the plurality of transducers 210 are added and then amplified once, instead of being amplified separately.

Examples of specific structures of the adding unit 222 are described in FIG. 8A to FIG. 8C and FIG. 9.

Figure 8A:
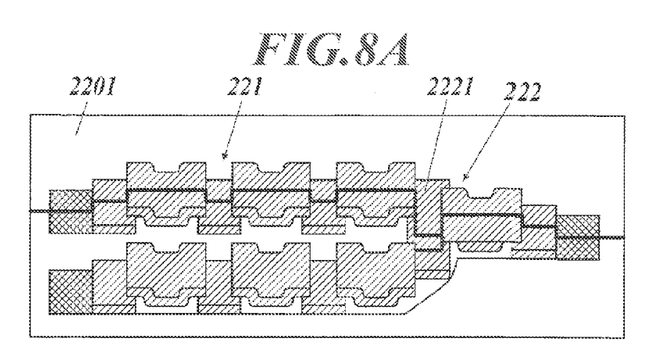
FIG. 8A is a diagram schematically showing an adding unit configured as one with a delay charge transferring unit.
Figure 8B:
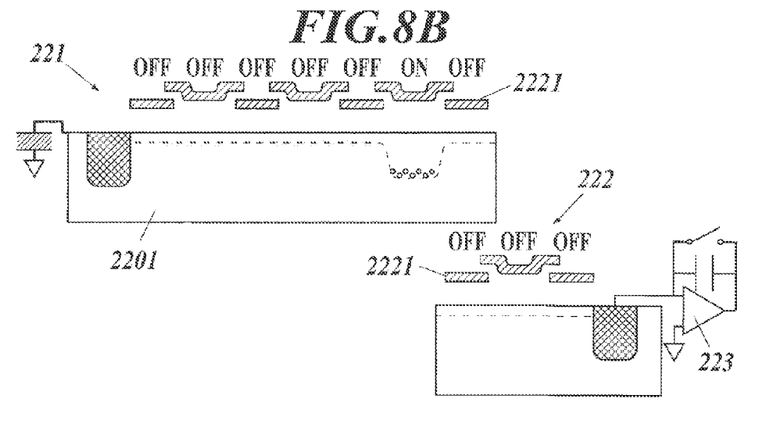
FIG. 8B is a diagram schematically showing a principle of operation where charge is transferred for each channel by a transfer electrode.
Figure 8C:
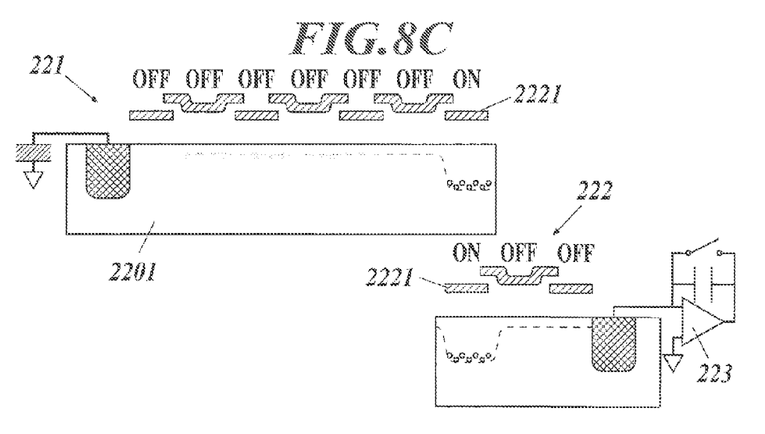
FIG. 8C is a diagram schematically showing a principle of operation where charge of an adjacent channel is transferred by the adding electrode and added.

FIG. 8A is a schematic diagram showing an example of a structure where the adding unit 222 is configured as one with the CCD 221 which is the delay charge transferring unit. According to the present embodiment, similar to the transfer of charge by the CCD 221, the charge transferred by the plurality of CCD 221 is transferred by an adding electrode 2221 which spreads to an adjacent channel and the charge is added. FIG. 8B and FIG. 8C are diagrams schematically showing the operation principle of the present embodiment. FIG. 8B shows a state of the charge being transferred in each channel by the transfer electrode. FIG. 8C shows a state of the charge of the adjacent channel being transferred by the adding electrode 2221 and the charge being added.

Figure 9:
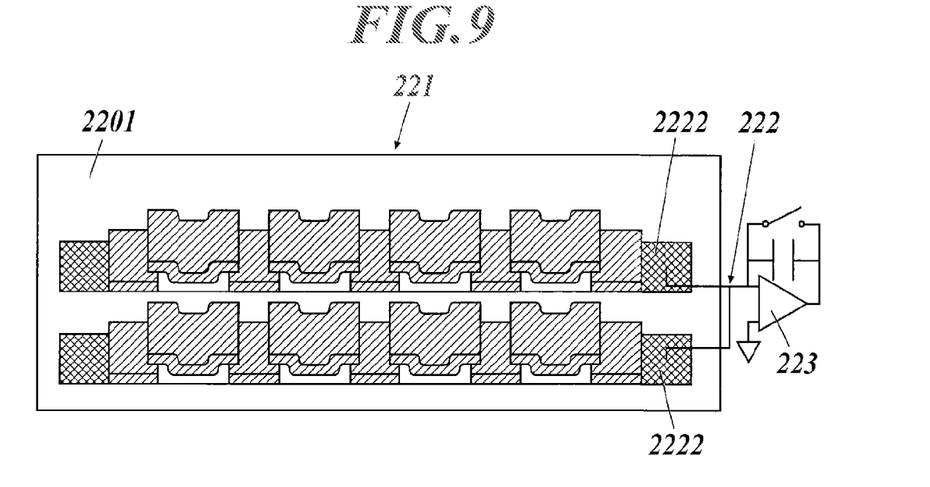
FIG. 9 is a diagram schematically showing another example of an adding unit.

FIG. 9 is a schematic diagram showing a different embodiment of the adding unit 222. According to the present embodiment, after the charge is transferred for each channel by the transfer electrode of the CCD 221, the charge is extracted from an NSD 2222 (implant region of N+) as electric current, and added in the adding amplifier (LNA 223). The LNA 223 can be configured on a same substrate with the CCD 221 as one semiconductor chip or the LNA 223 can be a circuit independent from the CCD 221.

As described above, the phasing adder 220 of the present embodiment includes the CCD 221 and the adding unit 222. The charge amount of the charge induced in the electrode 212 according to the amount of charge generated by the input ultrasound in each transducer 210 including the piezoelectric body 211 in which the charge is generated according to the sound pressure of the input ultrasound is obtained as is without amplifying as the signal charge by the CCD 221, and the CCD 221 holds the above for a predetermined amount of time. The signal charge is held in the CCD 221 for a predetermined amount of time where delay time occurs and the adding unit 222 processes with phasing adding the charge amount of the signal charge. In other words, in the phasing adder 220, each charge signal obtained from each transducer 210 is not amplified and it is possible to reduce the electric power consumption generated in the conventional operation of the low noise amplifier provided corresponding to the large number of transducers 210. On the other hand, the phasing adding is executed on the charge signal obtained from each transducer 210 as is. Therefore, the ratio of the heat noise with respect to the charge signal level can be reduced and the SNR can be enhanced. Consequently, the electric power consumption can be suppressed and the accuracy of the detection data can be maintained.

Specifically, the charge is directly introduced as signal charge to the CCD 221 from the N-type region 2202 according to the charge amount induced in the electrodes 212 and 213 provided in the transducer 210. Therefore, the signal according to the sound pressure of the ultrasound detected in each transducer 210 can be obtained by a configuration which is simple and in which the loss is small.

By using the CCD 221 (here, three phase CCD), according to the pattern of sequentially applying voltage to transfer electrodes 2217a to 2219a, 2217b, and 2218b, the signal charge is introduced in the potential well formed in the lower region of the transfer electrode in the semiconductor substrate 2201, the signal charge is moved a predetermined number of times among the potential wells, and then the signal charge is read out and the charge amount is transmitted to the adding unit 222. With this, it is possible to achieve low noise, low cost, and easily suppress electric power consumption by using a conventionally known configuration to detect ultrasound.

The ultrasound probe 2 of the present embodiment includes the phasing adder 220, the transducer 210 connected to the phasing adder 220, the LNA 223 which amplifies the charge amount processed with phasing adding as the voltage signal, and the communication unit 25 which outputs the data signal of the amplified voltage signal. In other words, the LNA 223 which enhances the signal level and the S/N ratio is provided one for each piece of data processed with phasing adding. Therefore, compared to providing the LNA 223 for each transducer 210, the accurate ultrasound detecting data can be obtained efficiently while reducing the electric power consumption. Moreover, according to the above, the amount of heat generation in the ultrasound probe 2 can be reduced. Therefore, it is possible to prevent the ultrasound probe 2 from rising to a temperature which is not suitable for live body examination.

The data after executing phasing adding is transmitted to the ultrasound diagnostic apparatus main body 1. Therefore, the unnecessary increase of data transfer amount can be prevented without reducing the accuracy of the obtained image.

The communication unit 25 is a wireless communication unit which outputs the data signal to the ultrasound diagnostic apparatus main body 1 by wireless communication such as wireless LAN or BLUETOOTH communication. Therefore, ultrasound examination can be done easily without being bothered by the length or position of the cable.

Specifically, in the ultrasound probe 2 which transfers data by wireless communication in which data transfer amount is limited, processing which consumes large amount of power such as signal amplifying is omitted while executing suitable data processing necessary for ultrasound diagnosis. Therefore, the data transfer amount can be reduced.

The apparatus further includes a transmitting unit 23 which outputs ultrasound with a predetermined wavelength from the transducer 210, and a transmitting/receiving switching unit 28 which connects the transducer 210 with either one of the transmitting unit 23 or the phasing adder 220 of the receiving unit 22 according to a control signal from the driving control unit 24. Therefore, the transducer 210 can be used for both transmitting and receiving the ultrasound, and the increase of the size of the ultrasound probe 2 can be prevented.

Second Embodiment

Next, the ultrasound probe of the second embodiment is described.

Figure 6A:
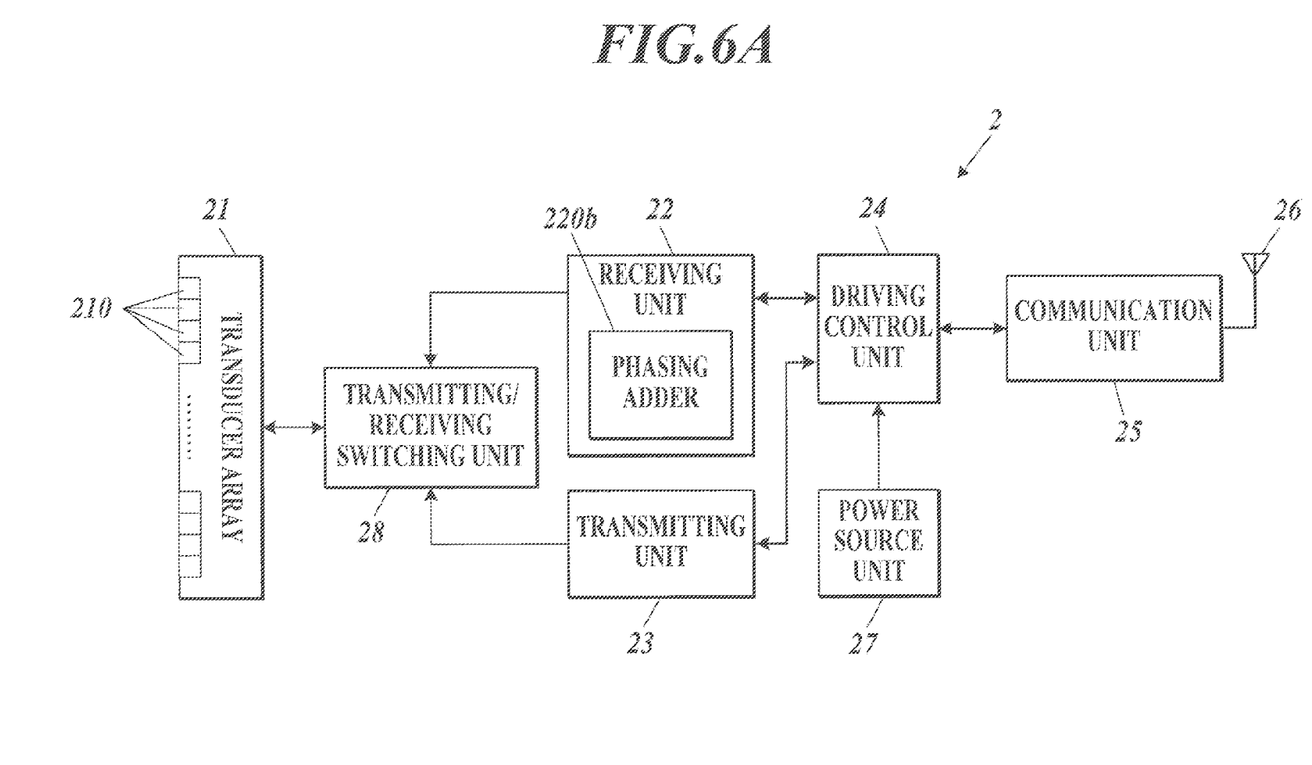
FIG. 6A is a block diagram showing an internal configuration of an ultrasound probe according to a second embodiment.
Figure 6B:
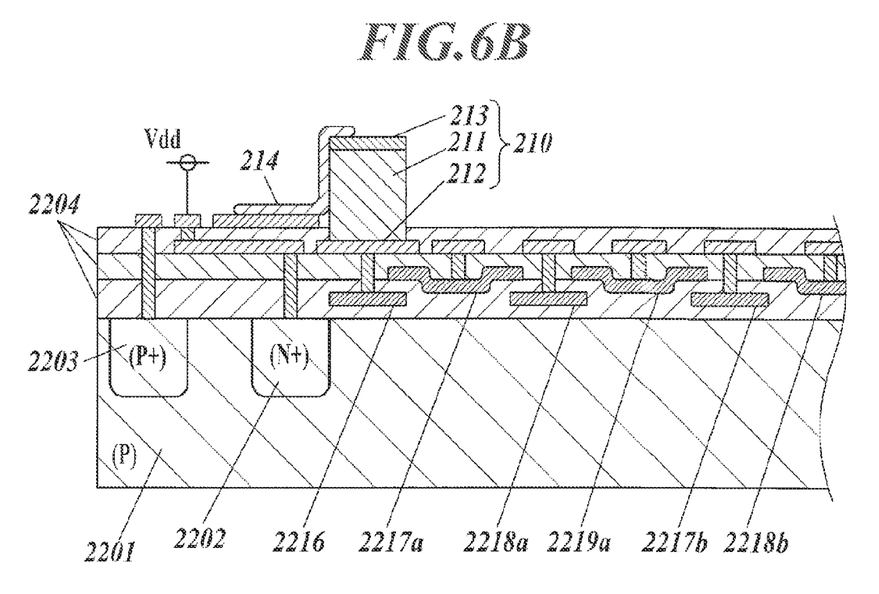
FIG. 6B is a diagram describing reception of ultrasound by the ultrasound probe according to a second embodiment.

FIG. 6A is a block diagram describing an internal configuration of the ultrasound probe 2 of the second embodiment. FIG. 6B is a cross-sectional view describing the configuration of receiving the ultrasound by the phasing adder 220b of the ultrasound probe 2 of the second embodiment.

As shown in FIG. 6A, the ultrasound probe 2 of the present embodiment is the same as the ultrasound probe 2 of the first embodiment with the exception of the phasing adder 220 of the first embodiment being replaced by the phasing adder 220b. Therefore, the same reference numerals are applied to the same components and the description is omitted.

As shown in FIG. 6B, the phasing adder 220b of the present embodiment is the same as the phasing adder 220 of the first embodiment with the exception of the following, the IG electrode 2216 (gate electrode) is connected to the electrode 212 provided in one edge of the piezoelectric body 211 and the N-type region 2202 (source region) of the semiconductor substrate 2201 is connected to the power source Vdd (bias voltage generating unit) of the power source unit 27. Therefore, the same reference numerals are applied to the same components and the description is omitted. Here, the switching unit includes the IG electrode 2216 and the N-type region 2202.

In the phasing adder 220b of the present embodiment, the ultrasound is input in the transducer 210 and the piezoelectric body 211 deforms due to the sound pressure. When the charge is generated, the potential of the electrode 212 and the IG electrode 2216 changes with respect to the grounded electrode 213. With this, a channel is formed below the IG electrode 2216, and conduction occurs between the N-type region 2202 and the potential well of the first transfer electrode 2217a in the CCD 221.

A voltage pulse (here, a square wave) is output in a cycle from the power source Vdd. With this, electrons are supplied to the N-type region 2202, and the supplied electrons pass through the channel below the IG electrode 2216 to be transferred to the potential well of the lower portion of the transfer electrode 2217a. The output cycle of this pulse voltage is set corresponding to the detecting target ultrasound frequency, in other words, the timing that the channel is formed and the charge is able to flow.

Here, the charge in about the charge amount induced in the electrodes 212 and 213 is introduced in the phasing adder 220b. In other words, in the ultrasound probe 2 of the present embodiment, the charge amount input to the fusing adder 220b is not amplified, and there is no need to set the power source Vdd to a voltage higher than necessary compared to the grounding voltage. With such voltage setting, the increase of the electric power consumption can be suppressed.

As described above, the ultrasound probe 2 of the second embodiment includes the phasing adder 220b. The phasing adder 220b is provided with the IG electrode 2216, and the N-type region 2202 connected to the power source Vdd which generates the predetermined bias voltage in the power source unit 27. The IG electrode 2216 is connected to one electrode 212 provided in the inducer 210, and the conduction state between the N-type region 2202 and the region of the CCD 221 is determined based on the potential of the IG electrode 2216 which changes according to the charge generated in the piezoelectric body 211. Therefore, even if the signal according to the input of the ultrasound is not amplified, the suitable analog electric signal can be obtained, and the sum of the charge of the electric signal is processed by phasing adding so as to be able to perform accurate ultrasound diagnosis. In other words, the phasing adder 220b and the ultrasound probe 2 can save electric power consumption regarding amplifying by LNA, and the power consumption can be reduced efficiently.

The power source Vdd applies the bias voltage synchronized with the cycle of change of the charge amount in the piezoelectric body 211 according to the frequency of the input ultrasound, in other words, the cycle that the channel is formed by the IG electrode 2216. Therefore, the maximum charge amount which can be flown by the IG electrode 2216 can be set to a predetermined value, and the accurate charge amount can be output to the CCD 221.

Third Embodiment

Next, the ultrasound probe of the third embodiment is described.

Figure 7A:
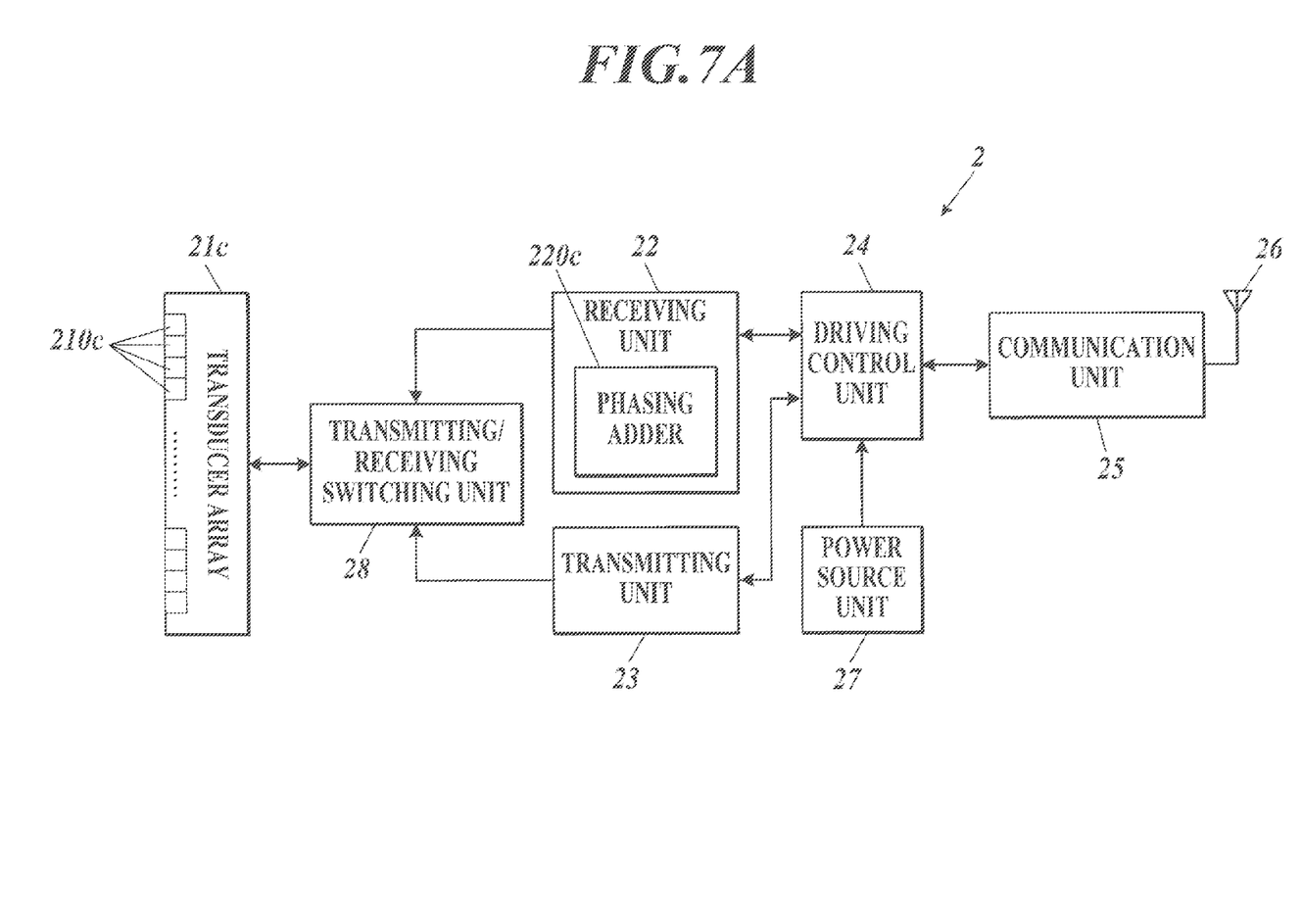
FIG. 7A is a block diagram showing an internal configuration of an ultrasound probe according to a third embodiment.
Figure 7B:
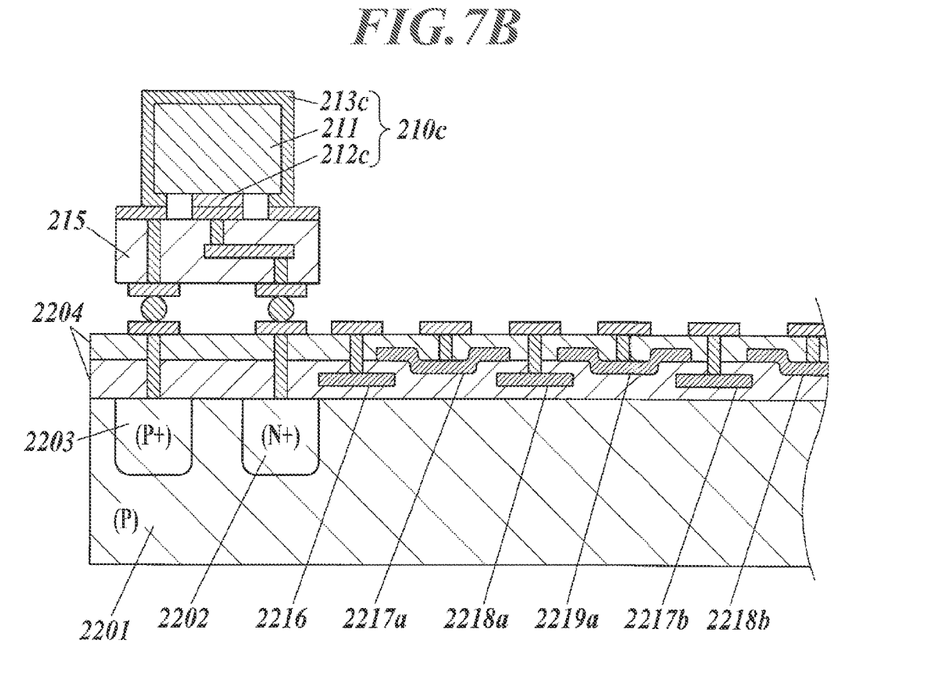
FIG. 7B is a diagram describing reception of ultrasound by the ultrasound probe according to a third embodiment.

FIG. 7A is a block diagram showing an internal configuration of the ultrasound probe 2 of the third embodiment. FIG. 7B is a diagram describing the configuration of reception when the ultrasound is received by the phasing adder 220c included in the ultrasound probe 2 of the third embodiment.

As shown in FIG. 7A, the ultrasound probe 2 of the present embodiment is the same as the ultrasound probe 2 of the first embodiment with the exception of the transducer array 21 and the phasing adder 220 in the probe 2 of the first embodiment being replaced by the transducer array 21c and the phasing adder 220c. Therefore, the same reference numerals are applied to the same components, and the description is omitted.

The transducer array 21c in the ultrasound probe 2 of the present embodiment includes the transducer 210c. As shown in FIG. 7B, in the transducer 210c, the electrodes 212c and 213c of both edges of the piezoelectric body 211 are each connected to the N-type region 2202 and the P-type region 2203 of the semiconductor substrate 2201 through the interposer substrate 215. The configuration of other portions is the same as the configuration of the ultrasound probe 2 of the first embodiment, and the same reference numerals are applied to the same components, and the description is omitted.

The interposer substrate 215 is a well-known interposer, such as a Si interposer. The size of the piezoelectric body 211 of the transducer 210c is set according to the ultrasound frequency to be detected and sensitivity. Turning to the circuit of the semiconductor substrate 2201, the circuit can be formed in a size determined according to cost. Therefore, by placing the interposer substrate 215 in between, it is possible to design and form the transducer array 21c and the semiconductor substrate 2201 separately. It is preferable that the connecting line formed in the interposer substrate 215 is positioned so that the electric signal transmitted to the N-type region 2202 is not attenuated more than necessary and that parasitic capacitance does not occur as much as possible between adjacent lines. In other words, the interposer substrate 215 is formed with a length, material, and lines so that the transmission percentage of the electric signal from the transducer 210c to the semiconductor substrate 2201 is a predetermined percentage (for example, 50%) or more.

As described above, the ultrasound probe 2 of the third embodiment includes an interposer substrate 215, and the circuit of the phasing adder 220c provided in the semiconductor substrate 2201 is connected to the electrodes 212c and 213c of the transducer 210c through the interposer substrate 215. Therefore, the transducer 210c and the phasing adder 220c can be made separately, and then the ultrasound probe 2 can be assembled using the interposer substrate 215. Therefore, it is possible to improve the yield of the ultrasound probe 2.

Since the transducer array 21c and the phasing adder 220c in which different pitches are demanded are manufactured separately, the design and the manufacturing can be performed more easily. Therefore, it is easy to reduce costs.

The present invention is not limited to the above embodiments and various changes are possible.

For example, according to the above embodiment, the CCD (potential well) is used as the delay transfer path of the charge. Alternatively, for example, other configurations regarding delay transfer such as, BBD (Bucket Brigade Device) (capacitor) can be used.

According to the above embodiments, the ultrasound probe 2 which communicates by wireless communication with the ultrasound diagnostic apparatus main body 1 is described. However, the present embodiment is not limited to the above. For example, the present invention can be applied to the following so as to be able to reduce power consumption, for example, an ultrasound probe 2 connected with a wire, or an ultrasound receiving portion in an ultrasound diagnostic apparatus formed as one with a probe which directly outputs ultrasound from the ultrasound diagnostic apparatus main body 1 and detects the ultrasound.

According to the present embodiment, the same transducer 210 is used to execute both transmitting and receiving of the ultrasound. Alternatively, the transducer used to transmit the ultrasound and the transducer used to receive the ultrasound can be provided and operated independently. With this, it is possible to reduce the switching and it is possible to prevent the loss of the charge signal due to the parasitic capacity generated in the transmitting circuit in receiving.

According to the present embodiment, each unit of the ultrasound probe 2 is driven and operated based entirely on the control signal from the ultrasound diagnostic apparatus main body 1. Alternatively, the units can be controlled partly by the driving control unit 24.

In addition to non-destructive examination of live body and buildings, the ultrasound diagnostic apparatus S including the ultrasound probe 2 of the present invention can be used for various purposes such as ultrasound CT examination and photo-acoustic examination.

The details such as the specific configuration and positioning shown in the above embodiment can be suitably changed without leaving the scope of the present invention.

The entire disclosure of Japanese Patent Application No. 2013-144297 filed on Jul. 10, 2013 and Japanese Patent Application No. 2014-139424 filed on Jul. 7, 2014 including description, claims, drawings, and abstract are incorporated herein by reference in its entirety.

What is claimed is:
1. An ultrasound probe, comprising:
a phasing adder;
a plurality of piezoelectric elements connected to the phasing adder, each of the piezoelectric elements including a piezoelectric body to generate charge according to sound pressure of input ultrasound;
a signal amplifying unit which amplifies a charge amount processed by the phasing adder and generates an amplified voltage signal; and
a signal output unit which outputs the amplified voltage signal,
wherein the phasing adder comprises
a plurality of delay charge transferring units, wherein each of the delay charge transferring units obtains signal charge in an amount obtained without amplifying according to charge generated in a respective one of the plurality of piezoelectric elements, and the each of the delay charge transferring units holds the signal charge for a predetermined amount of time;
a delay adding unit which executes phasing adding of an amount of the signal charge held for the predetermined amount of time in the delay charge transferring units; and
a switching unit including respective input get electrodes for the each of the delay charge transferring units, the respective input get electrodes being actu- atable to provide a channel between a region in which the signal charge is accumulated by the respective one of the piezoelectric elements and a potential well of a first electrode of the each of the delay charge transferring units; and a substrate on which both the piezoelectric elements and the delay transferring units of the phasing adder are mounted.

2. The ultrasound probe of claim 1, wherein, the amount of the signal charge corresponds to charge amount induced in electrodes provided on edges of the piezoelectric body in which the charge is generated in the respective one of the piezoelectric elements.

3. The ultrasound probe of claim 1, wherein, each of the delay charge transferring units is a CCD.

4. The ultrasound probe of claim 1, wherein, each of the delay charge transferring units is connected to an electrode through an interposer, the electrode provided on the piezoelectric body in which the charge is generated in the respective one of the piezoelectric elements.

5. The ultrasound probe of claim 1, wherein, the signal output unit includes a wireless communication unit which outputs the signal to an external device wirelessly.

6. The ultrasound probe of claim 1, wherein the region of the each of the piezoelectric elements in which the signal charge is accumulated is disposed in the substrate.

7. The ultrasound probe of claim 3, wherein, the signal output unit includes a wireless communication unit which outputs the signal to an external device wirelessly.

8. The ultrasound probe of claim 4, wherein, the signal output unit includes a wireless communication unit which outputs the signal to an external device wirelessly.

9. The ultrasound probe of claim 1, further comprising:
a transmitting driving unit which outputs an ultrasound with a predetermined wavelength from the piezoelectric elements; and
a transmitting/receiving switching driving unit which selectively connects the piezoelectric elements to either one of the transmitting driving unit or the delay charge transferring unit according to a control signal.

10. The ultrasound probe of claim 5, further comprising:
a transmitting driving unit which outputs an ultrasound with a predetermined wavelength from the piezoelectric elements; and
a transmitting/receiving switching driving unit which selectively connects the piezoelectric elements to either one of the transmitting driving unit or the delay charge transferring unit according to a control signal.

11. The ultrasound probe of claim 6, wherein, the signal output unit includes a wireless communication unit which outputs the signal to an external device wirelessly.

12. The ultrasound probe of claim 6, wherein the region in which the signal charge is accumulated and the substrate form a diode structure with a P-N junction.

13. The ultrasound probe of claim 12, wherein each of the input get electrodes is provided on a side of the diode structure of a respective one of the plurality of piezoelectric elements in an insulating layer above the substrate.

14. The ultrasound probe of claim 13, wherein each of the delay charge transferring units includes a plurality of transfer electrodes including the first electrode, and the transfer electrodes of the each of the delay charge transferring units are arranged in the insulating layer above the substrate.

* * * * *